United States Patent [19]
Castor et al.

[11] Patent Number: 6,051,694
[45] Date of Patent: Apr. 18, 2000

[54] METHOD FOR SIZE REDUCTION OF PROTEINS

[76] Inventors: Trevor Percival Castor, 469 Mystic St., Arlington, Mass. 02174; Glenn Thomas Hong, 18 Wachusett View Dr., Westborough, Mass. 01581

[21] Appl. No.: 09/156,197

[22] Filed: Sep. 17, 1998

[51] Int. Cl.⁷ .................................................. A61K 37/00
[52] U.S. Cl. ......................... 530/418; 530/419; 530/420; 530/427
[58] Field of Search ................................... 530/418, 419, 530/420, 427

[56] References Cited

FOREIGN PATENT DOCUMENTS

0542314 A1  5/1993  European Pat. Off. .

*Primary Examiner*—Cecilia J. Tsang
*Assistant Examiner*—C. Delacroix-Muirhad

[57] ABSTRACT

Liquefied gases, compressed gases, and supercritical fluids are used to form protein particles without first dissolving the protein. The product material is expected to retain full activity and be devoid of residual processing chemicals such as solvents, salts, or surfactants.

9 Claims, 1 Drawing Sheet

METHOD FOR SIZE REDUCTION OF PROTEINS

FIELD OF THE INVENTION

The present invention is relevant to the biotechnology and pharmaceutical industries where it is sometimes desirable to reduce proteins to a size of less than 1 to 100 microns.

BACKGROUND OF THE INVENTION

An ongoing concern in the pharmaceutical and biotechnology industries is the administration of a steady dosage of a therapeutic agent. Conventional delivery methods such as pills or injections typically provide a large spike of drug that decays over a period of time until the next dosage. The main limitation of such a dosing regimen is that the optimum level of drug is only present in the patient for a very brief period of time. Shortly following administration of the drug, it will be present at too high a level. The level will then decay, passing briefly through the optimum point, and remain at a suboptimum level until the next dosage. For many indications, the preferred dosage profile is one of a constant level within the patient—a difficult problem outside a hospital setting. Thus, dosage forms that have a built in time-release mechanism are of strong interest to the pharmaceutical and biotechnology industries. Such formulations have the further advantage of decreased dosage frequency, as the carriers can be designed to release drug for periods of many hours to several months. In consequence, continual patient vigilance is not required, and patient compliance with the prescribed dosage regimen is improved. By maintaining optimal treatment parameters, a reduction in the overall amount of drug administered becomes possible.

In the formulation of controlled release therapeutics, it is frequently desirable to disperse the material into very fine, uniform particles. Such particles may then be advantageously incorporated into controlled-release delivery vehicles such as polymeric microspheres or implantable devices, or delivered to the lungs as an aerosol. With proteinaceous therapeutics, the generation of such fine particles is particularly problematic. Table 1 provides a summary of conventional processing methods and their drawbacks.

TABLE 1

Conventional Size Reduction Methods for Proteins

| Method | Drawbacks |
|---|---|
| Mechanical milling | Protein denaturation by mechanical shear and/or heat |
| Spray drying | Protein denaturation at gas-liquid interface and/or heat for solvent vaporization |
| Fluid energy grinding | High velocity gas can yield electrostatically charged powders, size reduction inefficient for soft proteinaceous powders |
| Lyophilization | Broad size distribution, protein specific applicability and protocols |
| Antisolvent precipitation | Protein denaturation by organic solvents, solvent removal, solvent residuals, particle size control difficult |
| Salt precipitation | Protein specific applicability, salt removal or contamination, particle size control difficult |

Over the past decade, it has been demonstrated that compressed gases, liquefied gases, and materials intermediate to gases and liquids known as supercritical fluids can be used to create fine, uniform powders. Materials of this type will generically be referred to as "critical fluids" even though in some cases they would be rigorously defined as a compressed or liquefied gas. Carbon dioxide is a good example of such a critical fluid, with a critical temperature of 31° C. and a critical pressure of 1070 psia. In some instances it is useful to alter the solvation properties of a critical fluid by adding small amounts of what are known as modifiers or entrainers. Examples of entrainers include ethanol, methanol and acetone. The definition of critical fluid is meant to include critical fluids containing modifiers. A critical fluid may also be comprised of a mixture of critical fluids.

A critical fluid displays a wide spectrum of solvation power because its density is strongly dependent on both temperature and pressure—temperature changes of tens of degrees or pressure changes by tens of atmospheres can change solubility by an order of magnitude or more. The readily adjusted solubility of compounds in critical fluids is the basis of a number of precipitation processes that have appeared in the literature. The technique of varying solubility to cause precipitation is limited, however, by the fact that the compound of interest must have significant solubility in the critical fluid for at least some temperature and pressure conditions. Many materials of interest, such as proteins and peptides, are too polar to dissolve to any extent in critical fluids and hence do not fulfill this criterion. It is this limitation that has led to the development of the gas antisolvent (GAS) technique, which name refers to the fact that compressed gases (or liquefied or supercritical gases) are used as antisolvents. In this method, a compressed fluid is added to a conventional organic liquid solvent containing the solute to be crystallized. If compressed gas is used as the antisolvent, its dissolution into the solvent is typically accompanied by a reduction in density and change in polarity of the solvent mixture, and consequently, a reduction of the liquid's solvation power relative to a particular substance. As a result, the mixture becomes supersaturated, which causes crystals to form. If a supercritical fluid or liquefied gas is used as the antisolvent, however, the mixture density may actually be greater than that of the neat solvent. In this case, precipitation is presumably caused primarily by the polarity change of the mixture. In the GAS crystallization process, it is essential that solids have low solubility in the selected compressed fluid.

The GAS technique has been used by a number of workers to produce protein particles. Table 2 provides a survey of this work, which in all cases utilized $CO_2$ as the antisolvent. In the studies of Yeo et al. and Winters et al. included in Table 2, retention of enzyme activity was monitored. Yeo et al. carried out in vivo testing of the supercritically processed insulin in rats, finding full retention of activity. Winters et al. carried out secondary structure analysis of their supercritically processed proteins using Raman and Fourier transform infrared spectroscopy and found major conformational changes. However, upon redissolution in aqueous solution, the proteins appeared to largely regain their native configuration. The conclusion to be drawn from these studies is that, for at least some proteins, exposure to critical fluids and shearing during decompression does no significant damage to the proteins.

While some success has been achieved with GAS, there is a need for a process that can create small protein particles without the need for dissolution in an organic solvent.

TABLE 2

Antisolvent Precipitation of Proteins Using Carbon Dioxide.

| Compound | MW kDa | Solvent | T, °C. | P, psia | Particle Size $\mu$m | Ref. |
|---|---|---|---|---|---|---|
| Insulin | 6 | Dimethylsulfoxide | 25, 35 | 1280 | 0–4 | a |
| Insulin | 6 | N,N-dimethyl formamide | 35 | 1280 | 0–4 | a |
| Insulin | 6 | 10% $H_2O$ in ethanol | 35 | 1340 | 0–5 | b |
| Catalase | 240 | 10% $H_2O$ in ethanol | 35 | 1340 | 1 | b |
| Insulin | 6 | Dimethylsulfoxide | 28–46 | 1350–2115 | 1–5 | c |
| Lysozyme | 14 | Dimethylsulfoxide | 27–45 | 1093–1713 | 1–5 | c |
| Trypsin | 23 | Dimethylsulfoxide | 27–47 | 1093–2026 | 1–5 | c |

References:
a - Yeo, S-D, Lim, G-B, Debenedetti, P. G. and Bernstein, H., Formation of Microparticulate Protein Powders Using a Supercritical Fluid Antisolvent, Biotechnology and Bioengineering, 41: 341–346, 1993.
b - Tom, J. W., Lim, G.-B., Debenedetti, P. G. and Prud'homme, R. K., Applications of Supercritical Fluids in the Controlled Release of Drugs, ACS Symposium Series 514, American Chemical Society, Washington, D.C., 1993.
c - Winters, M. A., B. L. Knutson, P. G. Debenedetti, H. G. Sparks, T. M. Przybycien, C. L. Stevenson and S. J. Prestrelski, Precipitation of Proteins in Supercritical Carbon Dioxide J. Pharm. Sci. 85: 586–594, 1996.

SUMMARY OF THE INVENTION

The disclosed process uses critical fluids to form small protein particles without first dissolving the material in a liquid solvent. The product material is expected to retain full activity and be devoid of residual processing chemicals such as solvents, salts, or surfactants. The energy necessary for the size reduction is derived from a rapid depressurization of critical fluid. The low temperature generated by the expansion of the critical fluid helps to preserve the chemical integrity of the protein and is an advantage over conventional grinding processes that generate heat. Other benefits of the process include:

Improved processes and products in the area of drug delivery, e.g., more uniform and extended release of therapeutic from microsphere carriers or more uniform aerosol formulations.

Improved product quality with no residual solvent or surfactant contamination.

Improved process economics due to simplification of the process train.

Environmental advantages due to elimination of the use of organic solvents.

DETAILED DESCRIPTION OF THE INVENTION

Figure 1:
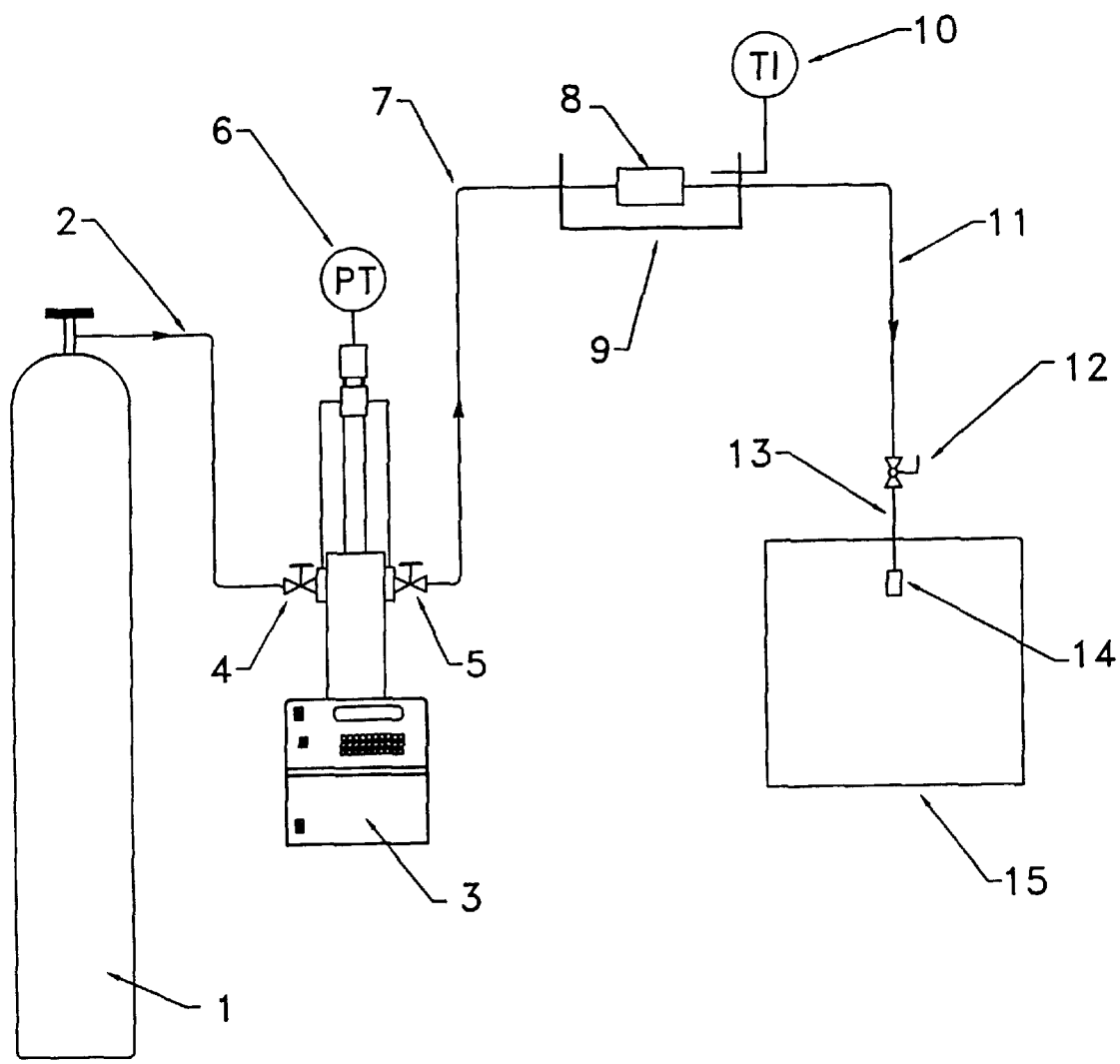
FIG. 1 depicts an apparatus suitable for carrying out the disclosed process.

With reference to FIG. 1, the desired amount of solid protein is manually loaded into contact chamber 8. The chamber is sealed and connected to the system between inlet line 7 and outlet line 11. To allow temperature control, the chamber 8 is immersed in temperature bath 9, instrumented with temperature indicator 10. Critical fluid contained in cylinder 1 is supplied through line 2 and valve 4 to high pressure pump 3. With valve 12 closed and valve 5 open, high pressure pump 3 pressurizes line 7, chamber 8, and line 11. Pressure is indicated by pressure transducer 6. Once chamber 8 has been pressurized, the protein and critical fluid are allowed a certain amount of contact time. After the desired contact time, valve 12 is quickly opened, e.g., in less than about 1 second, causing rapid depressurization of critical fluid with entrained protein into the depressurization receptacle 15. Depressurization may be carried out through a nozzle device 14, of which many designs are available. Some nozzle designs include impingement surfaces that increase mechanical shear by deflecting the discharging material. The depressurization receptacle 15 is substantially larger than the contact chamber and operates at only a low pressure. It may be open to the atmosphere via a filter, which would trap any potentially escaping particles, although this is not shown in the figure. Alternatively, depressurization receptacle 15 may be a flexible container such as a plastic bag. After depressurization, proteins are collected from the depressurization receptacle 15 for analysis.

As previously mentioned, critical fluids are not generally expected to solvate proteins. Comminution, however, does not require dissolution. The secondary and tertiary structure of proteins, and of protein aggregates, is partially dependent on hydrophobic interactions. If these interactions can be weakened by a surrounding and penetrating critical fluid, protein particles may become susceptible to breaking apart by the flow shear, mechanical impact, and expansion of the interstitial critical fluid which occur during rapid depressurization. Furthermore, breakage of the protein particles may be aided by the low temperatures resulting from the expansion process. The low temperatures may make the protein particles relatively brittle and susceptible to fracture.

EXAMPLES

The following examples illustrate the practice of the invention on an apparatus such as that shown in FIG. 1. For reference, the critical parameters of the fluids used are presented in Table 3.

TABLE 3

| | Critical Parameters of Fluids | |
|---|---|---|
| Fluid | $T_c$, °C. | $P_c$, psia |
| $N_2$ | −147 | 492 |
| $CO_2$ | 31.1 | 1070 |
| F-22 | 96.1 | 722 |
| $C_3H_8$ | 96.7 | 616 |

Materials:
Bovine Serum Albumin (BSA, MW=66,000); Sigma A-9647, 4% $H_2O$

Insulin (MW=6000); Sigma I-5500, from Bovine Pancreas, 6.9% $H_2O$
$CO_2$; Wesco UN1013
Propane; Associated Gas UN1978
Freon 22
Deionized water
Acetone; VWR, JT Baker 9005-03
Dry Ice Methods:

The general operation of the equipment was as described in the explanation of FIG. 1. The syringe pump 3 was filled with $CO_2$, propane, Freon 22 or $N_2$ and compressed to the operating pressure. The protein, typically about 0.35 g of BSA, was added to the contact chamber 8 (volume 11 mL), which was then connected to the outlet tube 11. The letdown ball valve 12 was shut. The pump was started at a constant pressure, which was determined for each particular run. The pump outlet valve 5 was opened and the critical fluid allowed to pressurize the system. The protein was contacted with critical fluid for a predetermined time, with the contact chamber 8 submerged in an acetone/dry ice, liquid nitrogen, or warm water bath 9 to control temperature. The pump outlet valve 5 was shut and then the letdown valve 12 was opened to decompress the contents of the unit in less than about 1 second into a depressurization bag. The samples were blown out through a 0.120 inch inside diameter nozzle. The samples were collected from the bag and viewed under a microscope to determine size using an eyepiece reticle.

Results and Discussion:

The examples given below illustrate the effect of some of the key parameters. The table columns specify the following parameters:

Experiment name
Contact chamber temperature in degrees Celsius
Contact chamber pressure in pounds per square inch gauge
Contact time τ in minutes
Approximate water content in weight percent
Target configuration—N signifies no impingement target, ¼" signifies a flat impingement target perpendicular to and ¼" from the nozzle tip.

Fluid used to treat the protein

Pretreatment used on the protein. Dried=dried in Savant centrifugal evaporator to about 0% moisture; 40° C.=dried in a vacuum oven at 40° C. to about 2% moisture; 80° C.=dried in a vacuum oven at 80° C. to about 0% moisture; lyophilized=dried in a Labconco freeze dryer evaporator to about 0% moisture; moistened=water added; ground=ground with glass stopper; reground=ground with a glass stopper twice; reprocessed=comminuted by the apparatus of FIG. 1 more than once.

Protein used. The initial BSA particles are approximately 50–500 μm, while the initial insulin particles range from 1.5–100 μm.

Resulting particle size in microns as determined by microscopic observation. The particle size ranges given account for at least approximately 90% of the particle mass.

Most of the following tables are broken into several sections, with each section providing a comparison for a different set of conditions.

Example 1. Effect of Temperature

Table 4 illustrates the effect of temperature on comminution of BSA. The first three table sections covering experiments with undried protein and carbon dioxide indicate that ambient temperature is most effective. The fourth section covering experiments with partially dried protein is somewhat ambiguous, while the last section of the table covering experiments with completely dried protein and nitrogen indicates that very low temperatures are less effective for particle size reduction. Thus, there appears to be no benefit to either heating or cooling for carrying out the comminution. It may nevertheless be desirable to cool the system for heat sensitive proteins.

TABLE 4

Effect of Temperature

| Expt. Name | T ° C. | P psi | τ min | $H_2O$ % | Target | Fluid | Pretreatment | Protein | Particle Size, μm |
|---|---|---|---|---|---|---|---|---|---|
| COM-25 | −50 | 1000 | 5 | 4 | 1/4" | $CO_2$ | None | BSA | 50–250 |
| COM-21 | 25 | 1000 | 5 | 4 | 1/4" | $CO_2$ | None | BSA | 50–300 |
| COM-23 | 50 | 1000 | 5 | 4 | 1/4" | $CO_2$ | None | BSA | 50–250 |
| COM-26 | −50 | 3000 | 5 | 4 | 1/4" | $CO_2$ | None | BSA | 50–500 |
| COM-22 | 25 | 3000 | 5 | 4 | 1/4" | $CO_2$ | None | BSA | 25–200 |
| COM-24 | 50 | 3000 | 5 | 4 | 1/4" | $CO_2$ | None | BSA | 50–500 |
| COM-51 | −50 | 3000 | 60 | 4 | 1/4" | $CO_2$ | None | BSA | 20–200 |
| COM-52 | 25 | 3000 | 60 | 4 | 1/4" | $CO_2$ | None | BSA | 25–125 |
| COM-49 | −68 | 3000 | 60 | 2 | 1/4" | $CO_2$ | 40° C. & Ground | BSA | 10–100 |
| COM-50 | −50 | 3000 | 60 | 2 | 1/4" | $CO_2$ | 40° C. & Ground | BSA | 20–200 |
| COM-47 | 20 | 3000 | 60 | 2 | 1/4" | $CO_2$ | 40° C. % Ground | BSA | 25–125 |
| COM-63 | −173 | 3000 | 60 | 0 | 1/4" | $N_2$ | Dried | BSA | 10–250 |
| COM-58 | 25 | 3000 | 60 | 0 | 1/4" | $N_2$ | Ground & Lyophilized | BSA | 2–25 |
| COM-59 | 25 | 3000 | 60 | 0 | 1/4" | $N_2$ | Lyophilized | BSA | 1–25 |

Example 2. Effect of Pressure

Table 5 illustrates the effect of pressure on comminution of BSA. The first section of the table, covering experiments with undried protein and carbon dioxide, indicates little effect of pressure. As shown by the other table sections, however, under most conditions pressure aids comminution. Even pressures as low as 400 psi give some size reduction, although pressures of at least 1000 psi are preferred. As shown in the last section of the table, with completely dried BSA a pressure of 1000 psi can give a significant amount of particles in the 1 μm size range.

TABLE 5

Effect of Pressure

| Expt. Name | T °C. | P psi | τ min | $H_2O$ % | Target | Fluid | Pretreatment | Protein | Particle Size, μm |
|---|---|---|---|---|---|---|---|---|---|
| COM-48 | 25 | 1000 | 60 | 4 | 1/4" | $CO_2$ | None | BSA | 25–100 |
| COM-52 | 25 | 3000 | 60 | 4 | 1/4" | $CO_2$ | None | BSA | 25–125 |
| COM-46 | −50 | 1000 | 60 | 2 | 1/4" | $CO_2$ | 40° C. & Ground | BSA | 50–300 |
| COM-50 | −50 | 3000 | 60 | 2 | 1/4" | $CO_2$ | 40° C. & Ground | BSA | 20–200 |
| COM-55 | 25 | 400 | 60 | 4 | 1/4" | $N_2$ | None | BSA | 25–250 |
| COM-54 | 25 | 600 | 60 | 4 | 1/4" | $N_2$ | None | BSA | 10–125 |
| COM-53 | 25 | 1000 | 60 | 4 | 1/4" | $N_2$ | None | BSA | 5–100 |
| COM-56 | 25 | 2000 | 60 | 4 | 1/4" | $N_2$ | None | BSA | 2–50 |
| COM-57 | 25 | 3000 | 60 | 4 | 1/4" | $N_2$ | None | BSA | 2–25 |
| COM-60 | 25 | 1000 | 60 | 0 | 1/4" | $N_2$ | Lyophilized | BSA | 1–100 |
| COM-59 | 25 | 3000 | 60 | 0 | 1/4" | $N_2$ | Lyophilized | BSA | 1–25 |

Example 3. Effect of Moisture

Table 6 illustrates the effect of moisture on comminution of BSA. Added moisture adversely affects comminution, while drying favors comminution of BSA.

TABLE 6

Effect of Moisture

| Expt. Name | T °C. | P psi | τ min | $H_2O$ % | Target | Fluid | Pretreatment | Protein | Particle Size, μm |
|---|---|---|---|---|---|---|---|---|---|
| COM-14 | 25 | 1000 | 5 | >5 | N | $CO_2$ | Moistened | BSA | 150–500 |
| COM-1 | 25 | 1000 | 5 | 4 | N | $CO_2$ | None | BSA | 50–300 |
| COM-53 | 25 | 1000 | 60 | 4 | 1/4" | $N_2$ | None | BSA | 5–100 |
| COM-60 | 25 | 1000 | 60 | 0 | 1/4" | $N_2$ | Lyophilized | BSA | 1–100 |
| COM-15 | 25 | 3000 | 5 | >5 | N | $CO_2$ | Moistened | BSA | 150–500 |
| COM-16 | 25 | 3000 | 5 | >5 | N | $CO_2$ | Moistened | BSA | 150–500 |
| COM-3 | 25 | 3000 | 5 | 4 | N | $CO_2$ | None | BSA | 25–250 |
| COM-57 | 25 | 3000 | 60 | 4 | 1/4" | $N_2$ | None | BSA | 2–25 |
| COM-59 | 25 | 3000 | 60 | 0 | 1/4" | $N_2$ | Lyophilized | BSA | 1–25 |

Example 4. Effect of Contact Time

Table 7 illustrates the effect of contact time on comminution of BSA. A contact time of more than 5 minutes is conducive to comminution.

Example 5. Effect of Pregrinding

Table 8 illustrates the effect of mechanical grinding prior to critical fluid treatment on comminution of BSA. Pregrinding helps slightly with the undried protein, but is unnecessary for the fully dried material.

TABLE 7

Effect of Contact Time

| Expt. Name | T °C. | P psi | τ min | $H_2O$ % | Target | Fluid | Pretreatment | Protein | Particle Size, μm |
|---|---|---|---|---|---|---|---|---|---|
| COM-35 | −50 | 3000 | 5 | 0 | 1/4" | $CO_2$ | Dried & Ground | BSA | 10–100 |
| COM-36 | −50 | 3000 | 15 | 0 | 1/4" | $CO_2$ | Dried & Ground | BSA | 1–75 |
| COM-37 | −50 | 3000 | 30 | 0 | 1/4" | $CO_2$ | Dried & Ground | BSA | 1–75 |
| COM-32 | −50 | 3000 | 120 | 0 | 1/4" | $CO_2$ | Dried & Ground | BSA | 1–75 |
| COM-26 | −50 | 3000 | 5 | 4 | 1/4" | $CO_2$ | None | BSA | 50–500 |
| COM-51 | −50 | 3000 | 60 | 4 | 1/4" | $CO_2$ | None | BSA | 20–200 |
| COM-21 | 25 | 1000 | 5 | 4 | 1/4" | $CO_2$ | None | BSA | 50–300 |
| COM-48 | 25 | 1000 | 60 | 4 | 1/4" | $CO_2$ | None | BSA | 25–100 |
| COM-22 | 25 | 3000 | 5 | 4 | 1/4" | $CO_2$ | None | BSA | 25–200 |
| COM-52 | 25 | 3000 | 60 | 4 | 1/4" | $CO_2$ | None | BSA | 25–125 |

TABLE 8

Effect of Pregrinding

| Expt. Name | T °C. | P psi | τ min | H₂O % | Target | Fluid | Pretreatment | Protein | Particle Size, μm |
|---|---|---|---|---|---|---|---|---|---|
| COM-51 | −50 | 3000 | 60 | 4 | 1/4" | $CO_2$ | None | BSA | 20–200 |
| COM-28 | −50 | 3000 | 60 | 4 | 1/4" | $CO_2$ | Ground | BSA | 25–175 |
| COM-1 | 25 | 1000 | 5 | 4 | N | $CO_2$ | None | BSA | 50–300 |
| COM-6 | 25 | 1000 | 5 | 4 | N | $CO_2$ | Ground | BSA | 25–250 |
| COM-59 | 25 | 3000 | 60 | 0 | 1/4" | $N_2$ | Lyophilized | BSA | 1–25 |
| COM-58 | 25 | 3000 | 60 | 0 | 1/4" | $N_2$ | Ground & Lyophilized | BSA | 2–25 |
| COM-3 | 25 | 3000 | 5 | 4 | N | $CO_2$ | None | BSA | 25–250 |
| COM-8 | 25 | 3000 | 5 | 4 | N | $CO_2$ | Reground | BSA | 25–250 |

Example 6. Effect of Impingement Target

Table 9 illustrates the effect of using an impingement target on comminution of BSA. An impingement target usually favors comminution.

TABLE 9

Effect of Impingement Target

| Expt. Name | T °C. | P psi | τ min | H₂O % | Target | Fluid | Pretreatment | Protein | Particle Size, μm |
|---|---|---|---|---|---|---|---|---|---|
| COM-10 | −50 | 1000 | 5 | 4 | N | $CO_2$ | None | BSA | 50–350 |
| COM-25 | −50 | 1000 | 5 | 4 | 1/4" | $CO_2$ | None | BSA | 50–250 |
| COM-1 | 25 | 1000 | 5 | 4 | N | $CO_2$ | None | BSA | 50–300 |
| COM-21 | 25 | 1000 | 5 | 4 | 1/4" | $CO_2$ | None | BSA | 50–300 |
| COM-3 | 25 | 3000 | 5 | 4 | N | $CO_2$ | None | BSA | 25–250 |
| COM-22 | 25 | 3000 | 5 | 4 | 1/4" | $CO_2$ | None | BSA | 25–200 |
| COM-12 | 50 | 1000 | 5 | 4 | N | $CO_2$ | None | BSA | 50–300 |
| COM-23 | 50 | 1000 | 5 | 4 | 1/4" | $CO_2$ | None | BSA | 50–250 |
| COM-13 | 50 | 3000 | 5 | 4 | N | $CO_2$ | None | BSA | 50–300 |
| COM-24 | 50 | 3000 | 5 | 4 | 1/4" | $CO_2$ | None | BSA | 50–500 |

Example 7. Effect of Fluid

Table 10 illustrates the effect of different treatment fluids on comminution of BSA. Nitrogen gives the best performance, followed by carbon dioxide. Freon-22 and propane are only marginally effective. The effectiveness of nitrogen suggests that air would also be a useful fluid, although some proteins may be sensitive to reaction with oxygen.

Example 8. Effect of Protein

Table 11 illustrates application of the comminution process to insulin and BSA. Insulin gives a much smaller particle size, no doubt at least partly due to its smaller initial size. The initial BSA particles are approximately 50–500 μm, while the initial insulin particles range from 1.5–100 μm. It is also of interest to note the relatively high moisture content of the insulin. Thus, depending on the results desired, drying of protein may not be necessary.

TABLE 10

Effect of Fluid

| Expt. Name | T °C. | P psi | τ min | H₂O % | Target | Fluid | Pretreatment | Protein | Particle Size, μm |
|---|---|---|---|---|---|---|---|---|---|
| COM-42 | −50 | 3000 | 60 | 0 | 1/4" | F-22 | Dried & Ground | BSA | 50–500 |
| COM-30 | −50 | 3000 | 60 | 0 | 1/4" | $CO_2$ | Dried & Ground | BSA | 1–150 |
| COM-38 | 25 | 1000 | 60 | 4 | 1/4" | $C_3H_8$ | None | BSA | 50–500 |
| COM-48 | 25 | 1000 | 60 | 4 | 1/4" | $CO_2$ | None | BSA | 25–100 |
| COM-53 | 25 | 1000 | 60 | 4 | 1/4" | $N_2$ | None | BSA | 5–100 |
| COM-52 | 25 | 3000 | 60 | 4 | 1/4" | $CO_2$ | None | BSA | 25–125 |
| COM-57 | 25 | 3000 | 60 | 4 | 1/4" | $N_2$ | None | BSA | 2–25 |

TABLE 11

Effect of Protein

| Expt. Name | T °C. | P psi | τ min | H₂O % | Target | Fluid | Pretreatment | Protein | Particle Size, μm |
|---|---|---|---|---|---|---|---|---|---|
| COM-30 | −50 | 3000 | 60 | 0 | 1/4" | CO₂ | Dried & Ground | BSA | 1–150 |
| COM-50 | −50 | 3000 | 60 | 2 | 1/4" | CO₂ | 40° C. & Ground | BSA | 20–200 |
| COM-28 | −50 | 3000 | 60 | 4 | 1/4" | CO₂ | Ground | BSA | 25–175 |
| COM-43 | −50 | 3000 | 60 | 6.9 | 1/4" | CO₂ | Ground | Insulin | 0.5–75 |

Example 9. Effect of Multiple Treatments

Table 12 illustrates the effect of multiple stage treatment on comminution of BSA. That is, protein which has already been processed by the invention is processed again. Reprocessing results in a small reduction in particle size.

TABLE 12

Effect of Multiple Treatments

| Expt. Name | T °C. | P psi | τ min | H₂O % | Target | Fluid | Pretreatment | Protein | Particle Size, μm |
|---|---|---|---|---|---|---|---|---|---|
| COM-30 | −50 | 3000 | 60 | 0 | 1/4" | CO₂ | Dried & Ground | BSA | 1–150 |
| COM-31 | −50 | 3000 | 60 | 0 | 1/4" | CO₂ | Reprocessed | BSA | 1–150 |
| COM-33 | −50 | 3000 | 60 | 0 | 1/4" | CO₂ | Reprocessed twice | BSA | 1–125 |
| COM-28 | −50 | 3000 | 60 | 4 | 1/4" | CO₂ | Ground | BSA | 25–175 |
| COM-29 | −50 | 3000 | 60 | 4 | 1/4" | CO₂ | Reprocessed | BSA | 10–150 |

The preceding examples are illustrative of the practice of the invention. Variations of the method will be apparent to those skilled in the art, and are considered to be within the scope of the invention. Examples of such variations include use of a cosolvent to help condition the protein prior to depressurization and operation of the process in a continuous as opposed to a batch mode.

What is claimed is:

1. A method for size reduction of protein in which solid protein is contacted with a critical fluid in which the protein is essentially insoluble, and the mixture of said protein and said critical fluid is subsequently depressurized.

2. The method of claim 1 in which the depressurization is accomplished in a period of less than about one second.

3. The method of claim 1 in which the depressurization is accomplished through a nozzle.

4. The method of claim 1 in which the critical fluid is nitrogen or carbon dioxide.

5. The method of claim 1 in which the contact time is more than 5 minutes.

6. The method of claim 1 in which the protein is dried prior to treatment.

7. The method of claim 1 in which the solid protein is contacted with a critical fluid having a pressure at least about 400 psi.

8. The method of claim 1 in which the solid protein is contacted with a critical fluid having a pressure at least about 1000 psi.

9. The method of claim 1 wherein the steps in which solid protein is contacted with a critical fluid and subsequently depressurized are performed at least two times.

* * * * *